(12) United States Patent
Liao et al.

(10) Patent No.: US 11,254,666 B2
(45) Date of Patent: Feb. 22, 2022

(54) COMPOUND AS GLS1 INHIBITOR

(71) Applicant: MEDSHINE DISCOVERY INC., Jiangsu (CN)

(72) Inventors: Yonggang Liao, Shanghai (CN); Chaonan Liu, Shanghai (CN); Changqing Wei, Shanghai (CN); Hao Wu, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 117 days.

(21) Appl. No.: 16/621,902

(22) PCT Filed: Jun. 13, 2018

(86) PCT No.: PCT/CN2018/091083
§ 371 (c)(1),
(2) Date: Jan. 10, 2020

(87) PCT Pub. No.: WO2018/228435
PCT Pub. Date: Dec. 20, 2018

(65) Prior Publication Data
US 2020/0216436 A1    Jul. 9, 2020

(30) Foreign Application Priority Data
Jun. 13, 2017 (CN) .......................... 201710444039.6

(51) Int. Cl.
*C07D 417/14* (2006.01)

(52) U.S. Cl.
CPC .................. *C07D 417/14* (2013.01)

(58) Field of Classification Search
CPC .................................................. C07D 417/14
USPC ..................................... 514/252.03
See application file for complete search history.

(56) References Cited

U.S. PATENT DOCUMENTS

| | | | |
|---|---|---|---|
| 9,783,533 B2 | 10/2017 | Bhavar et al. | |
| 10,040,788 B2 | 8/2018 | Finlay et al. | |
| 10,323,028 B2 | 6/2019 | Nissink et al. | |
| 2014/0194421 A1 | 7/2014 | Li et al. | |
| 2016/0297761 A1 | 10/2016 | Bhavar et al. | |
| 2016/0318921 A1 | 11/2016 | Bhavar et al. | |
| 2017/0152255 A1 | 6/2017 | Nissink et al. | |
| 2018/0057487 A1 | 3/2018 | Bhavar et al. | |
| 2019/0389853 A1 | 12/2019 | Nissink et al. | |

FOREIGN PATENT DOCUMENTS

| | | |
|---|---|---|
| CN | 104220070 A | 12/2014 |
| CN | 105051041 A | 11/2015 |
| CN | 105960405 A | 9/2016 |
| CN | 106029659 A | 10/2016 |
| CN | 106795150 A | 5/2017 |
| WO | WO-2015101957 A2 | 7/2015 |
| WO | 2016054388 A1 | 4/2016 |
| WO | WO-2017093299 A1 | 6/2017 |

OTHER PUBLICATIONS

The First Office Action regarding Application No. 18818915.3 dated Nov. 6, 2020.
The First Office Action regarding Application No. 2018800389637 dated Nov. 24, 2020.
Extended European Search Report regarding Application No. 18818915.3 dated Feb. 17, 2020.

*Primary Examiner* — Kahsay Habte
(74) *Attorney, Agent, or Firm* — Harness, Dickey & Pierce, P.L.C.

(57) ABSTRACT

A compound as a GLS1 inhibitor as represented by formula (I) or a pharmaceutically acceptable salt thereof.

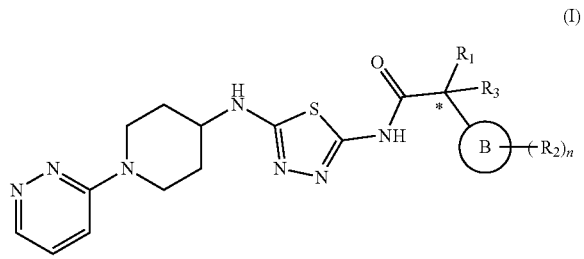

20 Claims, 1 Drawing Sheet

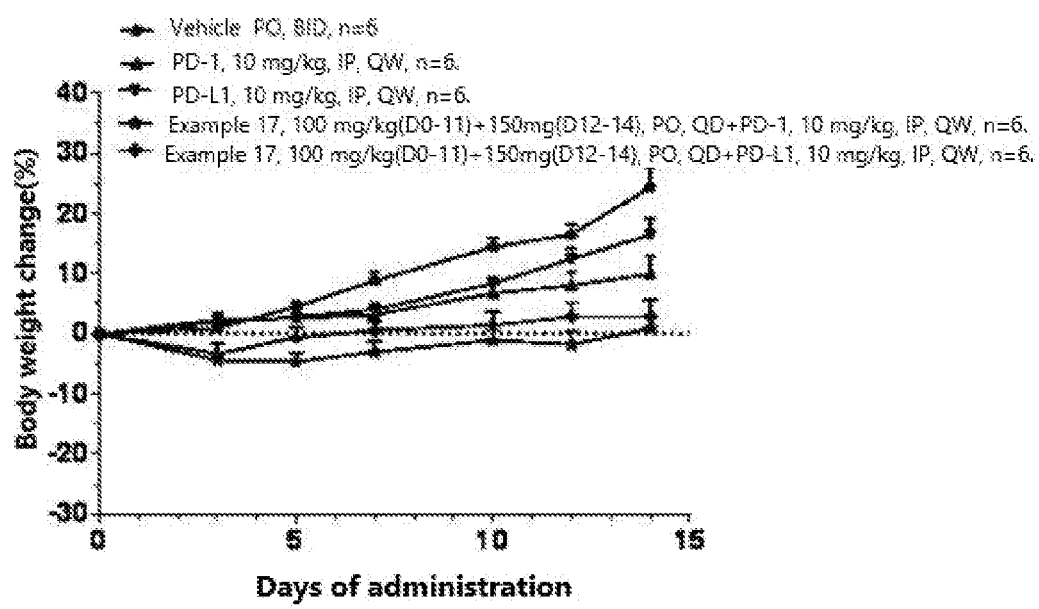

COMPOUND AS GLS1 INHIBITOR

CROSS-REFERENCE TO RELATED APPLICATIONS

The present application is a 371 National Phase of International Application No. PCT/CN2018/091083, filed Jun. 13, 2018, which claims the benefit of the Chinese Patent Application CN201710444039.6 filed on Jun. 13, 2017. The entire disclosures of the above applications are incorporated herein by reference.

FIELD OF INVENTION

The present invention relates to a novel class of compounds as GLS1 inhibitors, specifically, it relates to a compound represented by formula (I) or a pharmaceutically acceptable salt thereof.

PRIOR ARTS

Glutamine is the most abundant, non-essential amino acid in human body. Part of glutamine is taken up from circulation by amidation of glutamic acid and ammonia derived from purine metabolism, part of glutamine is produced by transamination of α-ketoglutarate derived from glucose and subsequent amidation. Glutaminase 1 (GLS1) can promote the decomposition of glutamine into glutamic acid and ammonium ions, and glutamic acid is subsequently converted into α-KG (α-ketoglutarate) by glutamic acid dehydrogenase, and then α-KG enters the TCA (tricarboxylic acid cycle) cycle to provide energy and macromolecular material sources. More importantly, the carbon source produced by glutamine metabolism supports the synthesis of OAA (oxaloacetate acid), acetyl-CoA and citric acid, and adipogenesis, while providing a nitrogen source to support the synthesis of purine, pyrimidine and DNA and NADPH (nicotinamide adenine dinucleotide phosphate) and GSH (glutathione) to maintain redox homeostasis. Glutamine acts as a precursor for the synthesis of many amino acids, proteins, nucleotides and other biologically important molecules.

Glutamine plays a key role in cell growth and proliferation. It is well known that cancer cells use glucose to produce ATP (adenosine-triphosphate) through aerobic glycolysis in a dissipative manner. At the same time, in order to meet rapid proliferation, cancer cells must use another energy source, glutamine oxidation phosphorylation, to produce ATP. Due to the continuous loss of citrate from the TCA cycle in proliferating cells, especially cancer cells, a large amount of TCA intermediates need to be supplemented, and glutamine consumption is increased for anabolic needs. Compared with normal tissues, glutamine demand is increased and consumption is accelerated in most cancer cells, and GLS1 activity is also much higher than in normal cells. The increased glutamine metabolism not only provides energy and substrate for the growth and proliferation of cancer cells, but also makes glutamine an effective candidate in cancer treatment.

Glutamine metabolism restriction can effectively inhibit cancer cells growth. As the first key enzyme for glutamine metabolism, GLS1 specific inhibitor can induce cell death in cancer cells. Two reported glutaminase inhibitors, CB-839 developed by Calithera Biosciences, and 968 compound developed by Cornell University, are in clinical trials.

At present, there is still a need to develop new glutaminase inhibitors for the treatment of diseases related to cell proliferation.

Content of the Present Invention

The present invention provides a compound represented by formula (I), an isomer thereof or a pharmaceutically acceptable salt thereof,

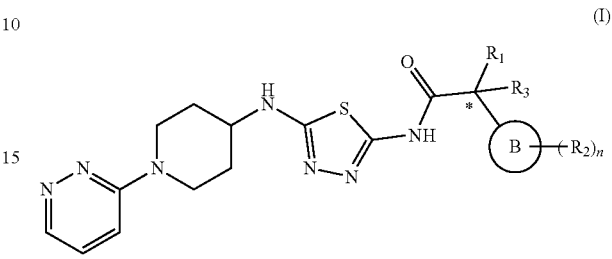

(I)

wherein, $R_1$ is selected from the group consisting of H, F, Cl, Br, I, OH, $NH_2$, $C_{1-6}$ alkyl and $C_{1-6}$ heteroalkyl, each of $C_{1-6}$ alkyl and $C_{1-6}$ heteroalkyl is optionally substituted by R, and the number of R is 1, 2 or 3;

$R_2$ is independently selected from the group consisting of H, F, Cl, Br, I, OH, $NH_2$, $C_{1-6}$ alkyl and $C_{1-6}$ heteroalkyl, each of $C_{1-6}$ alkyl and $C_{1-6}$ heteroalkyl is optionally substituted by R, and the number of R is 1, 2 or 3;

$R_3$ is selected from H; or $R_1$ and $R_3$ are linked together with the carbon atom to which they are attached form a $C_{3-6}$ cycloalkyl;

ring B is selected from phenyl and 5-6 membered heteroaryl;

n is selected from 0, 1, 2 or 3;

R is selected from the group consisting of H, F, Cl, Br, I, OH, $NH_2$, $C_{1-6}$ alkyl and $C_{1-6}$ heteroalkyl, each of $C_{1-6}$ alkyl and $C_{1-6}$ heteroalkyl is optionally substituted by R', and the number of R' is 1, 2 or 3;

R' is selected from F, Cl, Br, I, OH and $NH_2$;

when $R_1$ is selected from H, or $R_1$ and $R_3$ are linked together with the carbon atom to which they are attached form a $C_{3-6}$ cycloalkyl, then the carbon atom with "*" is not a chiral carbon atom;

when $R_1$ is not selected from H, then the carbon atom with "*" is a chiral carbon atom, and the compound represented by formula (I) exists in the form of a single enantiomer of (R) or (S) or is enriched in one enantiomer;

the "hetero" of the $C_{1-6}$ heteroalkyl and 5-6 membered heteroaryl is selected from the group consisting of N, —O—, —S— and —NH—; the above number of heteroatoms or heteroatom groups is independently selected from 1, 2, 3, or 4.

In some embodiments of the present invention, in the compound, the isomer thereof or the pharmaceutically acceptable salt thereof above, wherein, R is selected from the group consisting of H, F, Cl, Br, I, OH, $NH_2$ $C_{1-3}$ alkyl and $C_{1-3}$ alkoxyl, each of $C_{1-3}$ alkyl and $C_{1-3}$ alkoxyl is optionally substituted by R', and the number of R' is 1, 2 or 3.

In some embodiments of the present invention, in the compound, the isomer thereof or the pharmaceutically acceptable salt thereof above, wherein, R is selected from the group consisting of H, F, Cl, Br, I, OH, $NH_2$, Me, Et and

each of Me, Et and

is optionally substituted by R', and the number of R' is 1, 2 or 3.

In some embodiments of the present invention, in the compound, the isomer thereof or the pharmaceutically acceptable salt thereof above, wherein, R is selected from the group consisting of H, F, Cl, Br, I, OH, $NH_2$, Me, $CF_3$, Et,

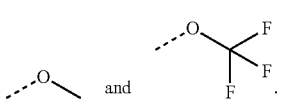

In some embodiments of the present invention, the above $R_1$ is selected from the group consisting of H, F, Cl, Br, I, OH, $NH_2$, $C_{1-3}$ alkyl and $C_{1-3}$ alkoxyl, each of $C_{1-3}$ alkyl and $C_{1-3}$ alkoxyl is optionally substituted by R, and the number of R is 1, 2 or 3.

In some embodiments of the present invention, the above $R_1$ is selected from the group consisting of H, F, Cl, Br, I, OH, $NH_2$, Me, $CF_3$, Et,

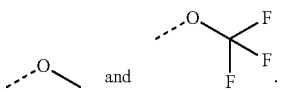

In some embodiments of the present invention, the above $R_2$ is independently selected from the group consisting of H, F, Cl, Br, I, OH, $NH_2$, $C_{1-3}$ alkyl and $C_{1-3}$ alkoxyl, each of $C_{1-3}$ alkyl and $C_{1-3}$ alkoxyl, is optionally substituted by R, and the number of R is 1, 2 or 3.

In some embodiments of the present invention, the above $R_2$ is independently selected from the group consisting of H, F, Cl, Br, I, OH, $NH_2$, Me, $CF_3$, Et,

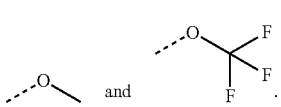

In some embodiments of the present invention, n is selected from 0, 1 or 2.

In some embodiments of the present invention, the above moiety

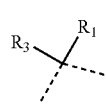

is selected from

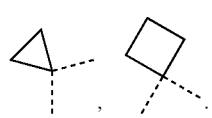

In some embodiments of the present invention, the above ring B is selected from: phenyl, pyridine.

In some embodiments of the present invention, the above moiety

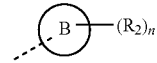

is selected from

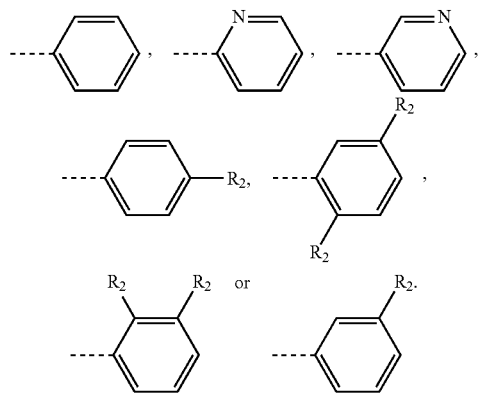

In some embodiments of the present invention, the above moiety

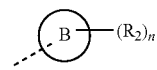

is selected from

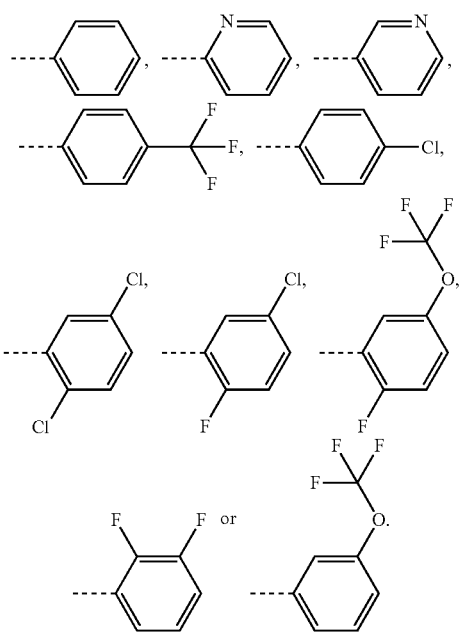

In some embodiments of the present invention, in the compound, the isomer thereof or the pharmaceutically acceptable salt thereof above, wherein, R is selected from the group consisting of H, F, Cl, Br, I, OH, NH$_2$, C$_{1-3}$ alkyl and C$_{1-3}$ alkoxyl, each of C$_{1-3}$ alkyl and C$_{1-3}$ alkoxyl is optionally substituted by R', and the number of R' is 1, 2 or 3, and other variables are as defined in the present invention.

In some embodiments of the present invention, in the compound, the isomer thereof or the pharmaceutically acceptable salt thereof above, wherein, R is selected from the group consisting of H, F, Cl, Br, I, OH, NH$_2$, Me, Et and

each of Me, Et and

is optionally substituted by R', and the number of R' is 1, 2 or 3, and other variables are as defined in the present invention.

In some embodiments of the present invention, the compound, the isomer thereof or the pharmaceutically acceptable salt thereof above, wherein, R is selected from the group consisting of H, F, Cl, Br, I, OH, NH$_2$, Me, CF$_3$, Et,

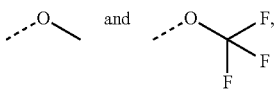

and other variables are as defined in the present invention.

In some embodiments of the present invention, the above R$_1$ is selected from the group consisting of H, F, Cl, Br, I, OH, NH$_2$, C$_{1-3}$ alkyl and C$_{1-3}$ alkoxyl, each of C$_{1-3}$ alkyl and C$_{1-3}$ alkoxyl is optionally substituted by R, and the number of R is by 1, 2 or 3, and other variables are as defined in the present invention.

In some embodiments of the present invention, the above R$_1$ is selected from the group consisting of H, F, Cl, Br, I, OH, NH$_2$, Me, CF$_3$, Et,

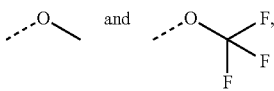

and other variables are as defined in the present invention.

In some embodiments of the present invention, the above R$_2$ is independently selected from the group consisting of H, F, Cl, Br, I, OH, NH$_2$, C$_{1-3}$ alkyl and C$_{1-3}$ alkoxyl, each of C$_{1-3}$ alkyl and C$_{1-3}$ alkoxyl is optionally substituted by R, the number of R is 1, 2 or 3, and other variables are as defined in the present invention.

In some embodiments of the present invention, the above R$_2$ is independently selected from the group consisting of H, F, Cl, Br, I, OH, NH$_2$, Me, CF$_3$,

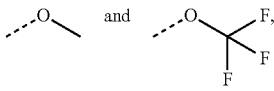

and other variables are as defined in the present invention.

In some embodiments of the present invention, the above n is selected from 0, 1 or 2, and other variables are as defined in the present invention.

In some embodiments of the present invention, the above moiety

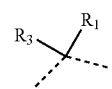

is selected from

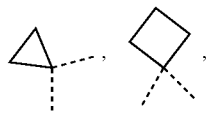

and other variables are as defined in the present invention.

In some embodiments of the present invention, the above ring B is selected from: phenyl, pyridine, and other variables are as defined in the present invention.

In some embodiments of the present invention, the above moiety

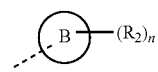

is selected from

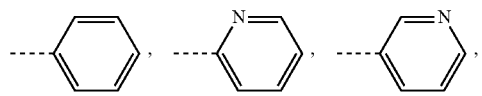

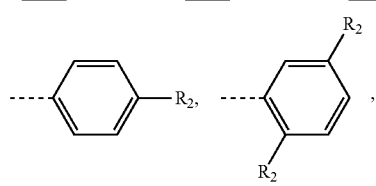

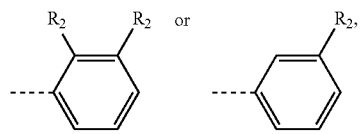

and other variables are as defined in the present invention.

In some embodiments of the present invention, the above moiety

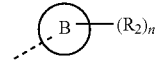

is selected from

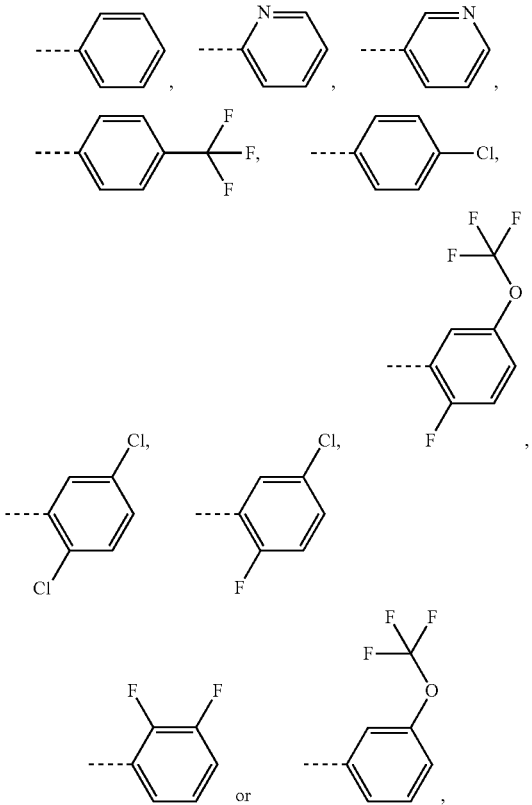

other variables are as defined in the present invention.

Some embodiments of the present invention are obtained by arbitrarily combining the above variables.

In some embodiments of the present invention, the compound, the isomer thereof or the pharmaceutically acceptable salt thereof above is selected from

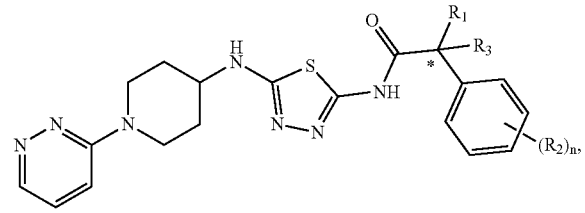
(I-1)

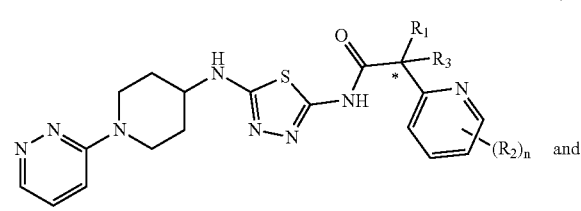
(I-2) and

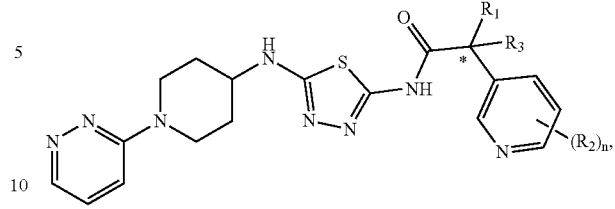
(I-3)

wherein, n, $R_1$, $R_2$, $R_3$ are as defined in the present invention.

When $R_1$ is selected from H, or $R_1$ and $R_3$ are linked together with the carbon atom to which they are attached form a $C_{3-6}$ cycloalkyl, then the carbon atom with "*" is not a chiral carbon atom;

when $R_1$ is not selected from H, then the carbon atom with "*" is a chiral carbon atom, and the compound represented by formula (I-1), (I-2) or (I-3) exists in the form of a single enantiomer of (R) or (S) or is enriched in one enantiomer.

The invention also provides the following compounds:

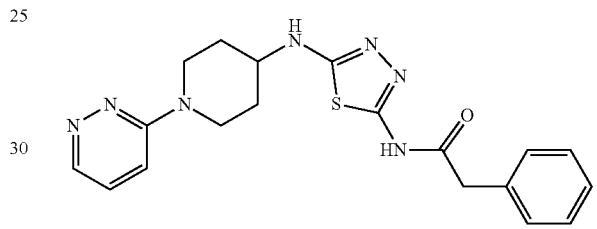

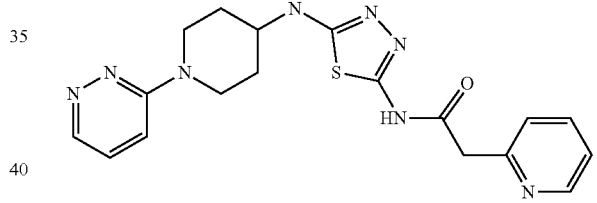

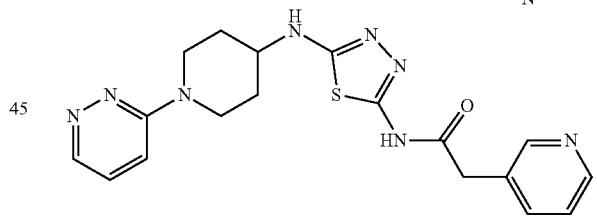

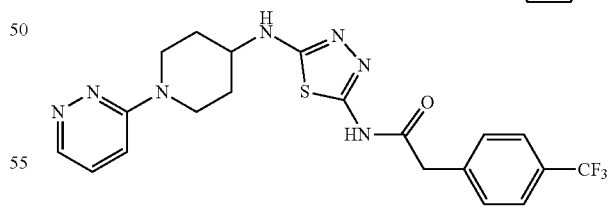

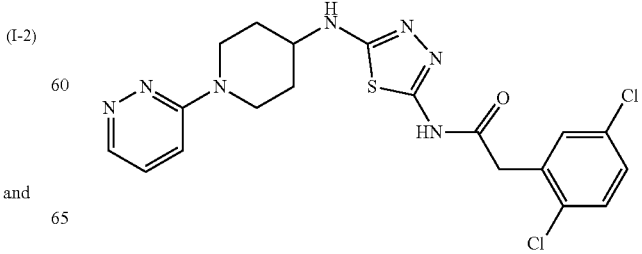

-continued
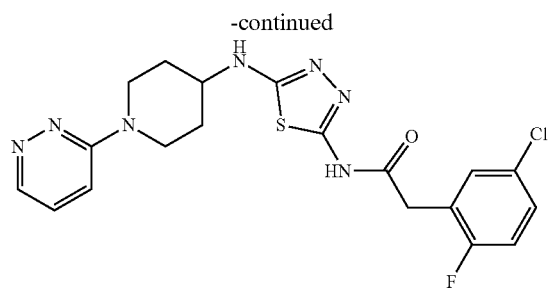
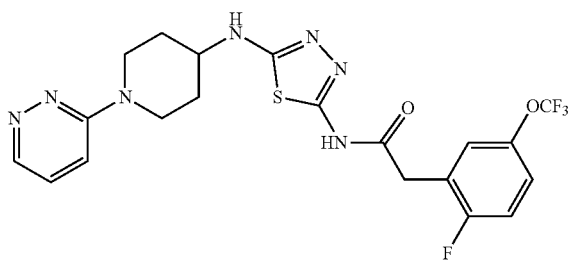
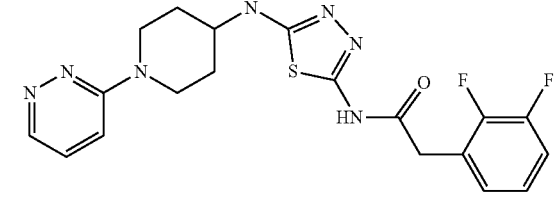
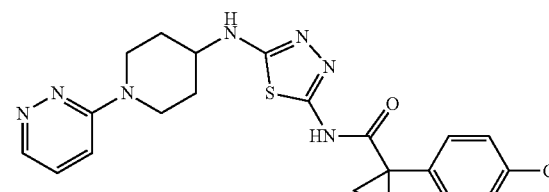
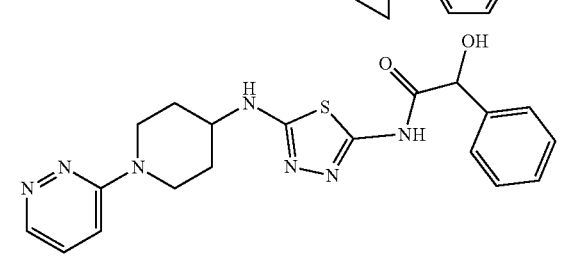
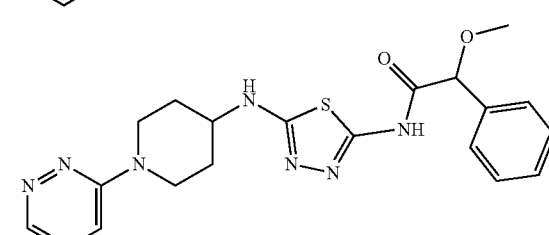
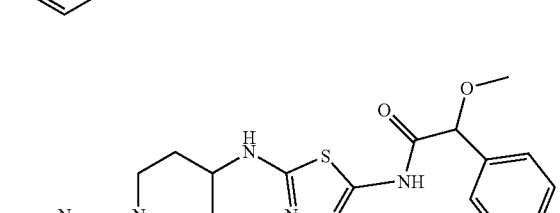
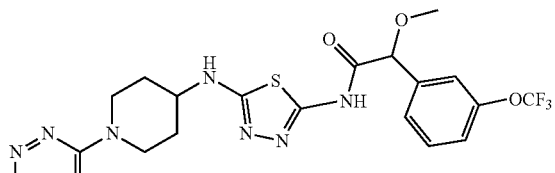
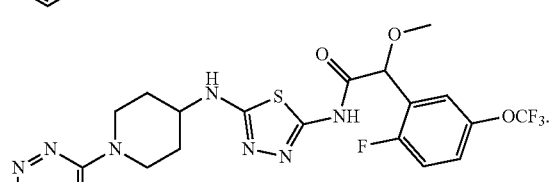
In some embodiments of the present invention, the compound above is selected from:
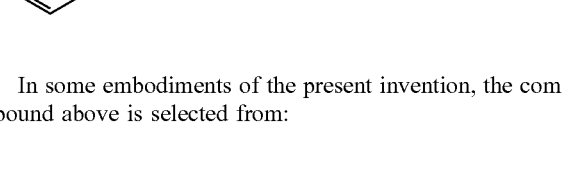
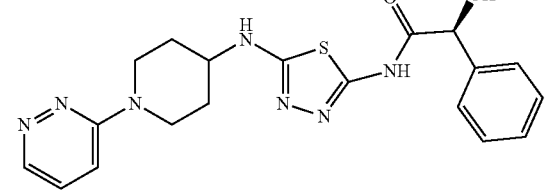
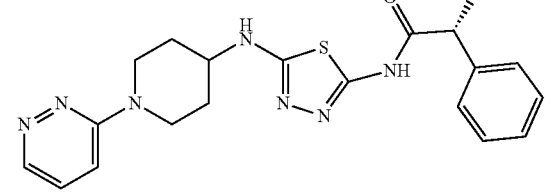
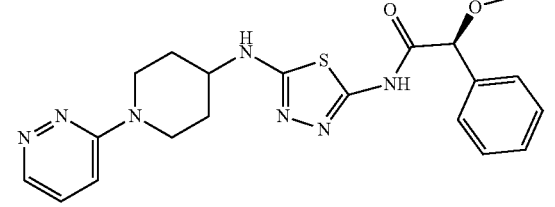
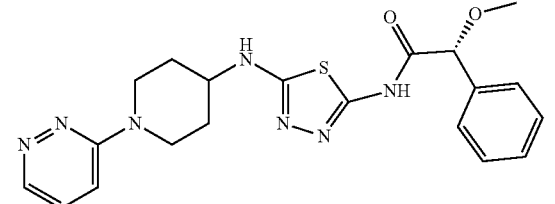

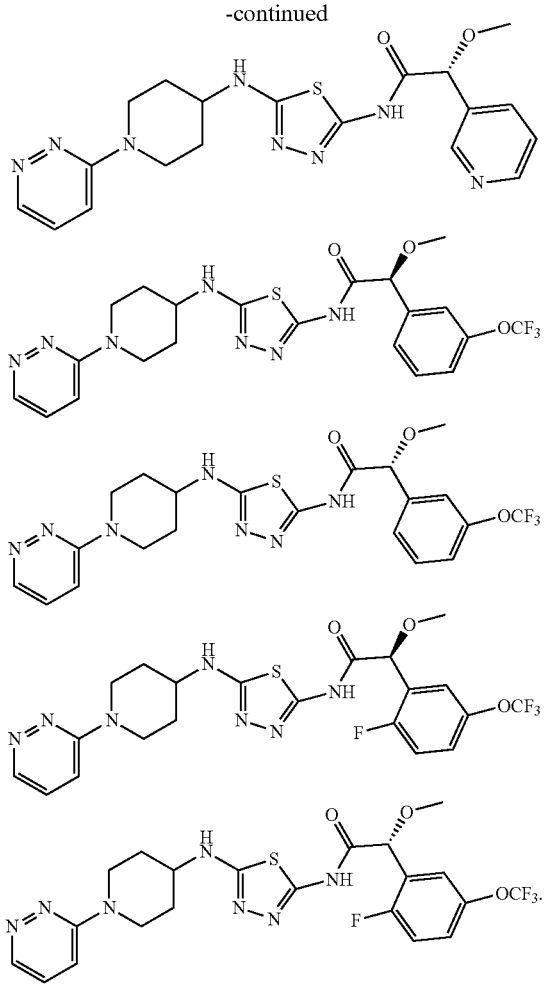

The present invention also provides a pharmaceutical composition, which comprises a therapeutically effective amount of the compound, or the pharmaceutically acceptable salt thereof above as an active ingredient, and a pharmaceutically acceptable carrier.

The present invention also provides a use of the compound or the pharmaceutically acceptable salt thereof above or the composition above for manufacturing a medicament for treating GLS1 inhibitor-related diseases.

Definition and Description

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present invention that contain both basic and acidic functional groups can be converted to any base or acid addition salt.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" stands for dextrorotation, "(L)" or "(−)" stands for levorotation, "(DL)" or "(±)" stands for racemization.

Unless otherwise specified, the absolute configuration of a stereogenic center is represented by a wedged solid bond (🖋) and a wedged dashed bond (⋰), and the relative configuration of a stereogenic center is represented by a straight solid bond (🖋) and a straight dashed bond (⋰). A wave line (∿) represents a wedged solid bond (🖋) or a wedged dashed bond (⋰), or represents a straight solid bond (🖋) or a straight dashed bond (⋰).

Unless otherwise specified, when a double bond structure exists in a compound, such as carbon-carbon double bond, carbon-nitrogen double bond, and nitrogen-nitrogen double bond, and each atom on the double bond is connected with two different substituents (in the double bond containing a nitrogen atom, a pair of lone electrons on the nitrogen atom is regarded as a substituent to which it is connected), if an atom on a double bond in the compound is connected with a wavy line (∿) to its substituent, it indicates the (Z) isomer, (E) isomer, or a mixture of the two isomers of the compound. For example, formula (A) indicates that the compound is in the form of a single isomer of formula (A-1) or formula (A-2) or a mixture of two isomers of formula (A-1) and formula (A-2); formula (B) indicates that the compound is in the form of a single isomer of formula (B-1) or formula (B-2) or a mixture of two isomers of formula (B-1) and formula (B-2). Formula (C) indicates that the compound is in the form of a single isomer of formula (C-1) or formula (C-2) or a mixture of two isomers of formula (C-1) and formula (C-2).

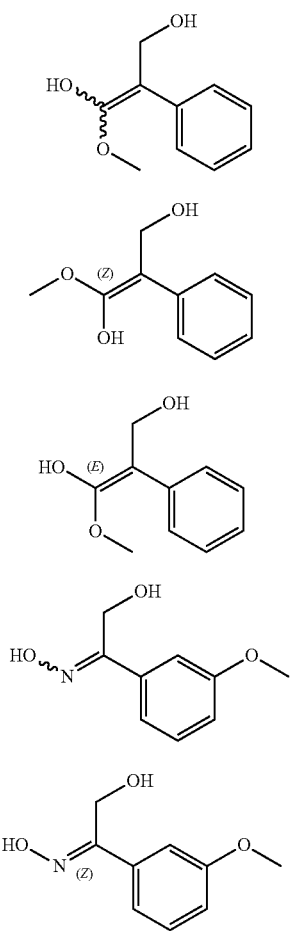

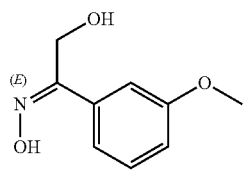

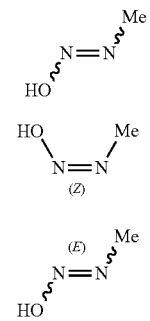

The compound of the present invention may be present in particular. Unless otherwise indicated, the term "tautomer" or "tautomeric form" refers to the fact that the different functional isomers are in dynamic equilibrium at room temperature and can be rapidly converted into each other. If tautomers are possible (such as in a solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the term "enriched in one isomer", "isomer enriched", "enriched in one enantiomer" or "enantiomer enriched" refers to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present invention, whether radioactive or not, are encompassed within the scope of the present invention. "Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom is(are) substituted with the substituent, including deuterium and hydrogen variants, as long as the valence of the specific atom is normal and the substituted compound is stable. When the substituent is an oxygen (i.e. =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative linking group does not indicate the direction for linking, the direction for linking is arbitrary, for example, the linking group L contained in

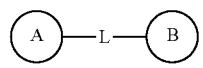

is -MW-, then -MW- can link ring A and ring B to form

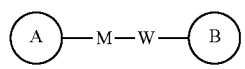

in the direction same as left-to-right reading order, and form

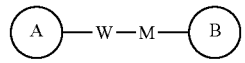

in the direction contrary to left-to-right reading order. Combinations of the linking groups, substituents and/or variants thereof are permissible only if such combinations result in stable compounds.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)$_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment. The total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and $S(O)_p$, p is 1 or 2). It is worth noting that the total number of S and O atom of an aromatic heterocycle is not more than one. The bridged ring is also included in the definition of the heterocycle. A bridged ring is formed when one or more than one atom (i.e., C, O, N or S) link two non-adjacent carbon or nitrogen atoms. A preferred bridged ring includes, but not limited to one carbon atom. Two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, Benzodihydropyranyl, chromene, cinnolinyl decahydroquinolinyl, 2H,6H-1,5,2-dithiazinyl, dihydrofuro[2,3-b] tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl, the aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl. Tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-$, $-S(O)-CH_3$, $-CH_2-CH_2-S(O)_2-CH_3$, $-CH=CH-O-CH_3$, $-CH_2-CH=N-OCH_3$ and $-CH=CH-N(CH_3)-CH_3$. Up to two consecutive heteroatoms can be present, such as, $-CH_2-NH-OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., $-CH_2F$) or poly-substituted (e.g., $-CF_3$), can be monovalent (e.g., methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g., one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

The solvent used in the present invention is commercially available. The present invention employs the following abbreviations: aq stands for water; HATU stands for O-(7-azabenzotriazol-1-yl)-N,N,N',N'-tetramethyluronium hexafluoro-phosphate; EDC stands for N-(3-dimethylaminopropyl)-N'-ethylcarbodiimide hydrochloride; m-CPBA stands for 3-chloroperoxybenzoic acid; eq stands for equivalent, equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for acetic acid esters; EtOH stands for ethanol; MeOH for methanol; CBz stands for benzyloxycarbonyl, an amine protecting group; BOC stands for t-butylcarbonyl is an amine protecting group; HOAc stands for acetic acid; NaCNBH$_3$ stands for sodium cyanoborohydride; r.t. stands for room temperature; O/N stands for overnight; THF stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride; CS$_2$ stands for carbon disulfide; TsOH stands for p-toluenesulfonic acid; NFSI stands for N-fluoro-N-(phenylsulfonyl) benzenesulfonamide; NCS stands for 1-chloropyrrolidine-2,5-dione; n-Bu$_4$NF stands for tetrabutylammonium; iPrOH stands for 2-propanol; mp stands for melting point; LDA stands for diisopropylamino lithium; EDTA stands for ethylenediaminetetraacetic acid; BSA stands for bovine serum albumin; DTT stands for DL-dithiothreitol; T3P stands for propylphosphonic anhydride.

Compounds are named manually or by ChemDraw® software, the commercially available compounds use their vendor directory names.

Compared with the existing GLS1 inhibitors, the compound of the present invention has significant GLS1 inhibitory effect, and has greatly improved solubility, metabolic stability, and efficacy, reduced toxicity, and significant or unexpected pharmaceutical potential.

BRIEF DESCRIPTION OF THE DRAWING

FIG. 1 shows the relative body weight change (%) of the test substance on female mouse C57/BL6 model of subcutaneously transplanted tumor of lung cancer 3LL cells.

IP: intraperitoneal injection; PO: oral administration; QW: once a week; QD: once a day.

The relative weight change is calculated based on the animal weight at the beginning of the dose. Data points represent the percentage change in average body weight within the group, and error bars represent standard error (SEM).

DETAILED DESCRIPTION OF THE PREFERRED EMBODIMENT

The following examples further illustrate the present invention, but the present invention is not limited thereto. The present invention has been described in detail in the text, and its specific embodiments have also been disclosed, for one skilled person in the art, it is obvious to modify and improve the embodiments of the present invention within the spirit and scope of the present invention.

Example 1&2: Compound 1&2

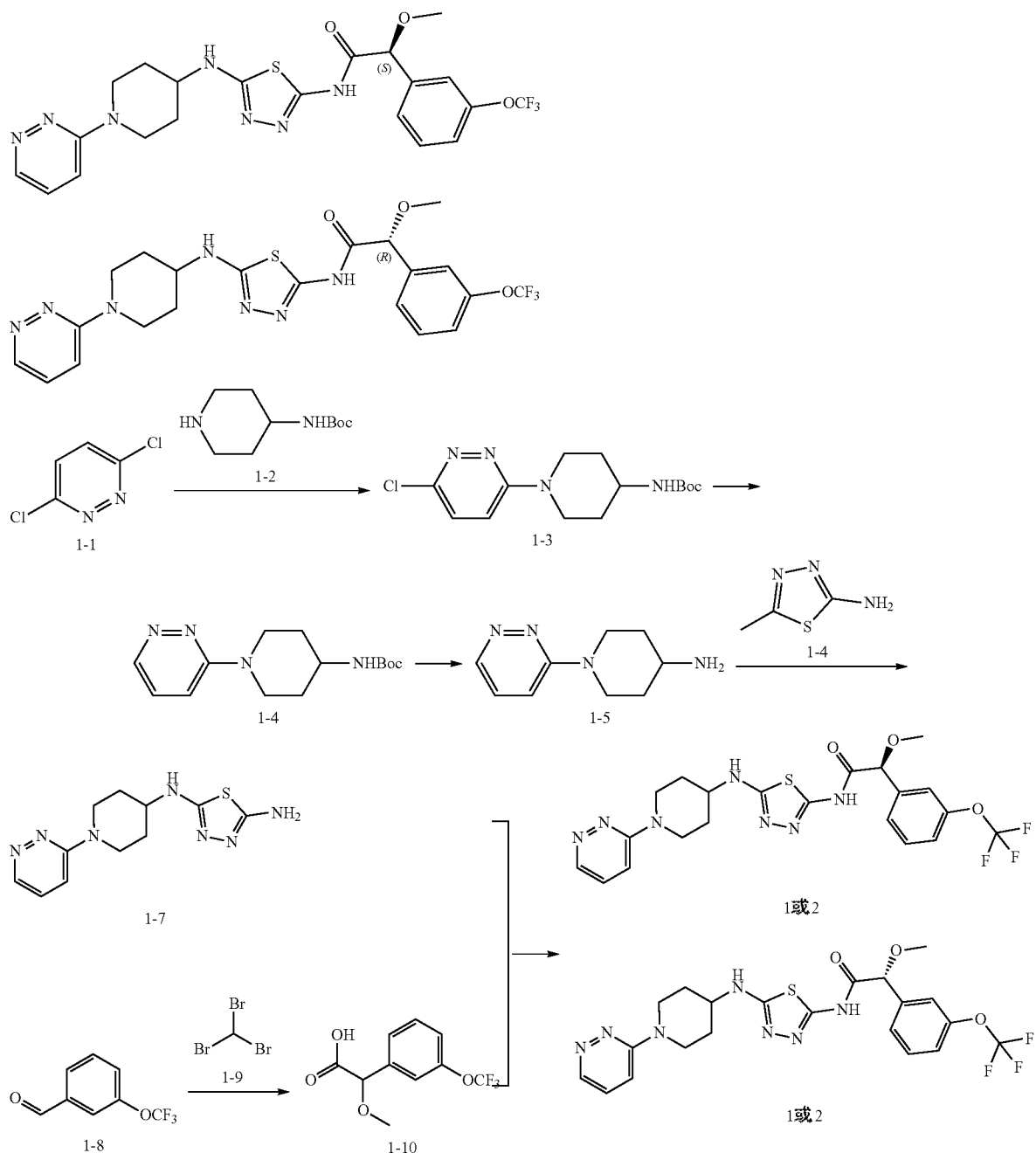

Step 1: Compound 1-1 (18 g, 120.82 mmol) and compound 2-2 (24.20 g, 120.82 mmol) were added to DMF (180 mL), then potassium carbonate (33.40 g, 241.65 mmol) was added, and the mixture was stirred at 100° C. for 3 hours. After the completion of the reaction, the mixture was extracted with ethyl acetate (100 mL*3) and water (100 mL). The organic phase was washed with saturated brine (400 mL), dried over anhydrous sodium sulfate and concentrated to obtain crude compound 1-3, which was used directly in the next step. MS ESI calculated $C_{14}H_{21}ClN_4O_2[M+H]^+$ 314, found 314.

Step 2: Compound 1-3 (7.4 g, crude product) was added to methanol (10 mL), then ammonium formate solid (14.92 g, 236.58 mmol) and 10% dry palladium on carbon (0.78 g) were added at 25° C., the mixture was stirred at 40° C. for 2 hours. After the completion of the reaction, the target compound 1-4 was directly filtered to obtain a crude product. MS ESI calculated $C_{14}H_{22}N_4O_2[M+H]^+$ 279, found 279.

Step 3: Compound 1-4 (7.1 g, crude product) was added to trifluoroacetic acid (10 mL), the mixture was stirred at 25° C. for 2 hours. After the completion of the reaction, the target compound 1-5 was directly concentrated to obtain a crude product. MS ESI calculated $C_9H_{14}N_4[M+H]^+$ 179, found 179.

Step 4: Compound 1-5 (4.5 g, crude product) and compound 1-6 (4.55 g, 25.25 mmol) were added to ethanol (45 mL), then sodium bicarbonate (12.73 g, 151.49 mmol) was added, and the reaction mixture was stirred at 90° C. for 2 hours. After the completion of the reaction, the reaction mixture was directly filtered and the solvent was evaporated to give crude compound 1-7. MS ESI calculated $C_{11}H_{15}N_7S$ [M+H]$^+$ 278, found 278.

Step 5: Potassium hydroxide (3.25 g, 57.86 mmol) was added to methanol (30 mL), and then the mixture was slowly added to a mixed solution of compound 1-8 (2 g, 10.52 mmol) and compound 1-9 (3.19 g, 12.62 mmol) in methanol (20 mL) at 0° C. The reaction was stirred at 25° C. for 19 hours. After the completion of the reaction, the reaction mixture was extracted with tert-butyl methyl ether (100 mL) and water (100 mL). The aqueous phase was acidified with dilute hydrochloric acid to pH=5, and then extracted with ethyl acetate (20 mL*3). The organic phase was washed with saturated brine (80 mL), dried over anhydrous sodium sulfate, followed by concentration, and the compound 1-10 was obtained by column chromatography (petroleum ether: ethyl acetate=1:1). $^1$H NMR (400 MHz, CHLOROFORM-d) δ ppm 3.47 (s, 3H), 4.83 (s, 1H), 7.23 (d, J=5.2 Hz, 1H), 7.35 (s, 1H), 7.40-7.44 (m, 2H), 10.38 (brs, 1H).

Step 6: Compound 1-7 (110.86 mg, 399.73 μmol), compound 1-10 (0.2 g, 799.45 μmol) and diisopropylethylamine (154.98 mg, 1.20 mmol) were added to DMF (2 mL), and then T3P (713.19 μL, 1.20 mmol, 50% purity) was added, the reaction mixture was stirred at 25° C. for 2 hours. After the completion of the reaction, the mixture was extracted with ethyl acetate (50 mL*3) and water (50 mL). The organic phase was dried over anhydrous sodium sulfate, concentrated and separated by preparative TLC (dichloromethane:methanol=20:1), and then resolved by chiral HPLC (chromatographic column: AD (250 mm*30 mm, 10 μm); mobile phase: [0.1% $NH_3H_2O$ IPA]; B %: 35%–35%) to give compound 1 or 2. MS ESI calculated $C_{21}H_{22}F_3N_7O_3S$ [M+H]$^+$ 510, found 510. Isomer 1 (Example 1) had a retention time of 5.87 minutes; $^1$H NMR (400 MHz, METHANOL-d$_4$) δ ppm 1.50-1.64 (m, 2H), 2.18 (br d, J=10.04 Hz, 2H), 3.17-3.29 (m, 2H), 3.49 (s, 3H), 3.88-3.93 (m, 1H), 4.33 (br d, J=13.55 Hz, 2H), 5.01 (s, 1H), 7.28-7.33 (m, 2H), 7.38-7.46 (m, 2H), 7.49-7.55 (m, 2H), 8.47 (d, J=3.51 Hz, 1H).

Isomer 2 (Example 2) had a retention time of 6.30 minutes; $^1$H NMR (400 MHz, METHANOL-d$_4$) δ ppm 1.51-1.63 (m, 2H), 2.18 (br d, J=10.04 Hz, 2H), 3.18-3.27 (m, 2H), 3.49 (s, 3H), 3.88-3.93 (m, 1H), 4.33 (br d, J=13.55 Hz, 2H), 5.01 (s, 1H), 7.27-7.33 (m, 2H), 7.38-7.46 (m, 2H), 7.48-7.55 (m, 2H), 8.47 (d, J=3.51 Hz, 1H).

The compounds shown in Table 1 can be prepared in a similar method to compound 1 or 2:

TABLE 1

Commercial chiral carboxylic acid preparations were used in those examples with unspecified chiral retention times

| Example | Structure | LCMS |
|---|---|---|
| 3 | 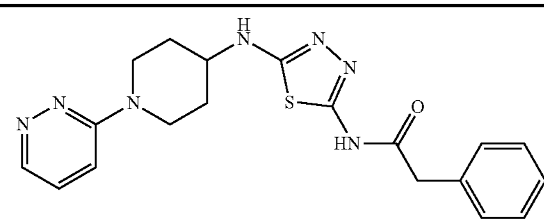 | MS ESI calculated $C_{19}H_{21}N_7OS$ [M + H]$^+$ 396, found 396. |
| 4 | 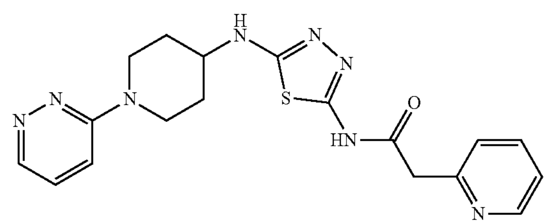 [SMILES: O=C(Cc1ccccn1)Nc1nnc(NC2CCN(c3cccnn3)CC2)s1] | $^1$H NMR (400 MHz, METHANOL-d$_4$) δ ppm 1.51-1.63 (m, 2 H), 2.26-2.30 (m, 2 H), 3.46-3.52 (m, 2 H), 3.99-4.03 (m, 1 H), 4.04-4.38 (m, 2 H), 7.95-8.09 (m, 5 H), 8.64-8.65 (m, 1 H), 8.65-8.67 (m, 1 H), 8.48 (d, J = 4.00 Hz, 1 H). MS ESI calculated $C_{18}H_{20}N_8OS$ [M + H]$^+$ 397, found 397. |
| 5 | 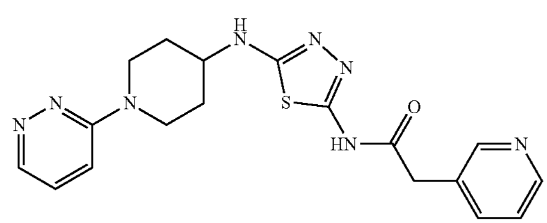 [SMILES: O=C(Cc1cccnc1)Nc1nnc(NC2CCN(c3cccnn3)CC2)s1] | MS ESI calculated $C_{18}H_{20}N_8OS$ [M + H]$^+$ 397, found 397. |
| 6 | 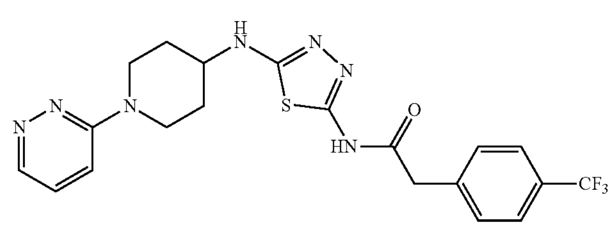 [SMILES: O=C(Cc1ccc(C(F)(F)F)cc1)Nc1nnc(NC2CCN(c3cccnn3)CC2)s1] | MS ESI calculated $C_{20}H_{20}F_3N_7OS$ [M + H]$^+$ 464, found 464. |

TABLE 1-continued

Commercial chiral carboxylic acid preparations were used in those examples with unspecified chiral retention times

| Example | Structure | LCMS |
|---|---|---|
| 7 | 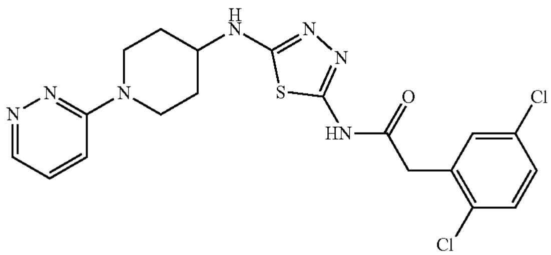 [SMILES: O=C(Cc1cc(Cl)ccc1Cl)Nc1nnc(NC2CCN(c3cccnn3)CC2)s1] | MS ESI calculated $C_{19}H_{19}Cl_2N_7OS$ $[M + H]^+$ 464, found 464. |
| 8 | 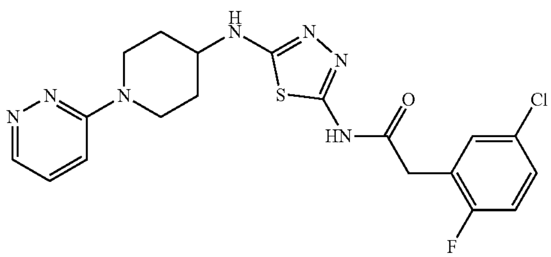 [SMILES: O=C(Cc1cc(Cl)ccc1F)Nc1nnc(NC2CCN(c3cccnn3)CC2)s1] | MS ESI calculated $C_{19}H_{19}ClFN_7OS$ $[M + H]^+$ 448, found 448. |
| 9 | 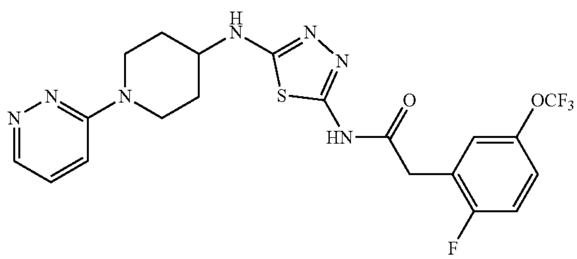 [SMILES: O=C(Cc1cc(OC(F)(F)F)ccc1F)Nc1nnc(NC2CCN(c3cccnn3)CC2)s1] | $^1$H NMR (400 MHz, METHANOL-d$_4$) δ ppm 1.72-1.83 (m, 2 H) 2.27 (br d, J = 10.04 Hz, 2 H), 3.41-3.52 (m, 2 H), 3.92-4.03 (m, 3 H), 4.38 (br d, J = 13.80 Hz, 2 H), 7.20-7.32 (m, 2 H), 7.33-7.39 (m, 1 H), 7.97 (dd, J = 9.79, 4.77 Hz, 1 H), 8.06-8.11 (m, 1 H) 8.67 (d, J = 4.52 Hz, 1 H). MS ESI calculated $C_{20}H_{19}F_4N_7O_2S$ $[M + H]^+$ 498, found 498. |
| 10 | 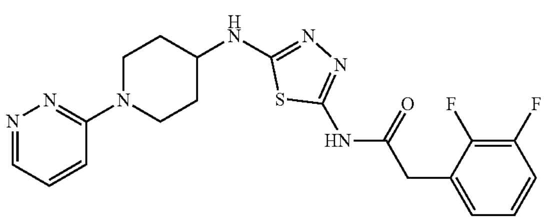 [SMILES: O=C(Cc1cccc(F)c1F)Nc1nnc(NC2CCN(c3cccnn3)CC2)s1] | MS ESI calculated $C_{19}H_{19}F_2N_7OS$ $[M + H]^+$ 432, found 432. |
| 11 | 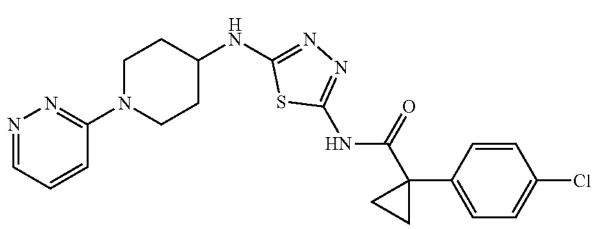 [SMILES: O=C(Nc1nnc(NC2CCN(c3cccnn3)CC2)s1)C1(c2ccc(Cl)cc2)CC1] | MS ESI calculated $C_{21}H_{22}ClN_7OS$ $[M + H]^+$ 456, found 456. |
| 12 | 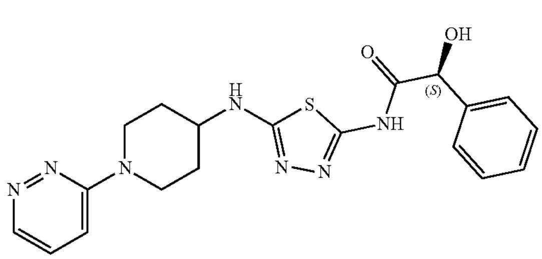 | MS ESI calculated $C_{19}H_{21}N_7O_2S$ $[M + H]^+$ 412, found 412. |

TABLE 1-continued

Commercial chiral carboxylic acid preparations were used in those examples with unspecified chiral retention times

| Example | Structure | LCMS |
|---|---|---|
| 13 | 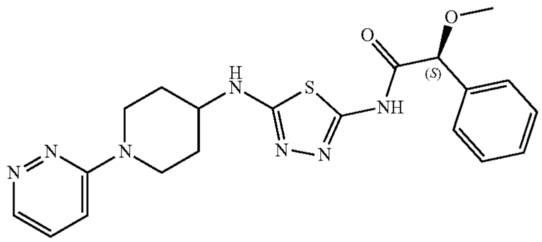 | ¹HNMR (400 MHz, METHANOL-d₄) δ ppm 1.97-2.00 (m, 2 H), 2.28-2.32 (m, 2 H), 3.41-3.49 (m, 5 H), 3.55-3.59 (m, 1 H), 4.44 (d, J = 13.60 Hz, 2 H), 5.01 (s, 1 H), 7.38-7.42 (m, 3 H), 7.49-7.51 (m, 2 H), 7.92-7.94 (m, 1 H), 8.04 (d, J = 9.20 Hz, 1 H), 8.61 (d, J = 4.40 Hz, 1 H). MS ESI calculated $C_{20}H_{23}N_7O_2S$ [M + H]⁺ 426, found 426. |
| 14 | 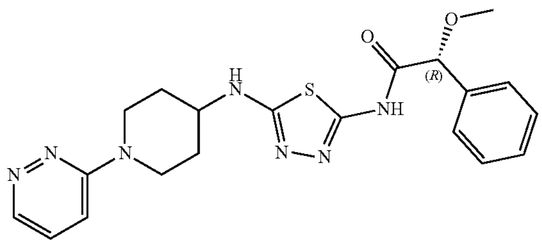 | ¹HNMR (400 MHz, METHANOL-d₄) δ ppm 1.94-2.02 (m, 2 H), 2.28-2.32 (m, 2 H), 3.41-3.48 (m, 5 H), 3.54-3.56 (m, 1 H), 4.43 (d, J = 14.80 Hz, 2 H), 5.01 (s, 1 H), 7.36-7.40 (m, 3 H), 7.49-7.51 (m, 2 H), 7.90-7.92 (m, 1 H), 8.04 (d, J = 9.20 Hz, 1 H), 8.61 (d, J = 4.40 Hz, 1 H). MS ESI calculated $C_{20}H_{23}N_7O_2S$ [M + H]⁺ 426, found 426. |
| 15 | 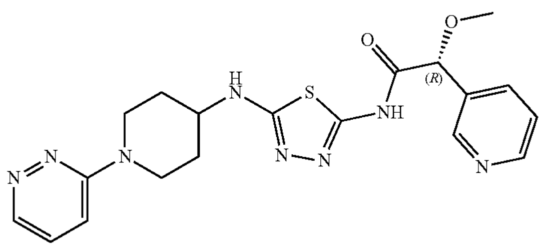 | MS ESI calculated $C_{19}H_{22}N_8O_2S$ [M + H]⁺ 427, found 427. (Chiral column: Chiralcel OJ 250*30 mm, 5 μm; mobile phase: [0.1% NH₃H₂O MeOH]; B % 45%-45%, 4.86 minutes. |
| 16 | 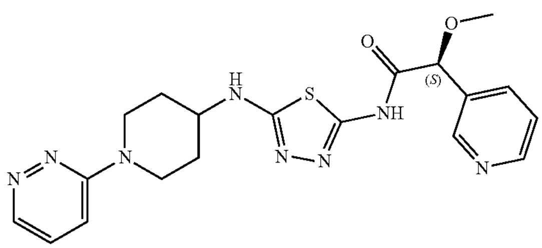 | MS ESI calculated $C_{19}H_{22}N_8O_2S$ [M + H]⁺ 427, found 427. (Chiral column: Chiralcel OJ 250*30 mm, 5 μm; mobile phase: [0.1% NH₃H₂O MeOH]; B %: 45%-45%, 5.52 minutes. |
| 17 | 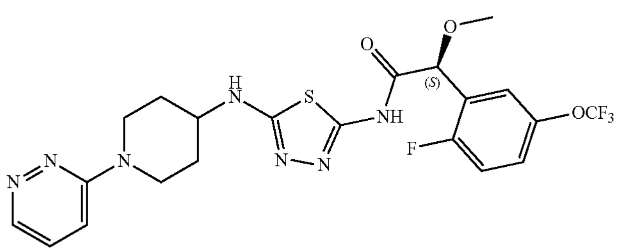 | ¹HNMR (400 MHz, METHANOL-d₄) δ ppm 1.53-1.63 (m, 2 H), 2.19 (d, J = 10.00 Hz, 2 H), 3.20-3.27 (m, 2 H), 3.49 (s, 3 H), 3.89-3.94 (m, 1 H), 4.34 (d, J = 15.60 Hz, 2 H), 5.28 (s, 1 H), 7.29-7.33 (m, 2 H), 7.36-7.40 (m, 2 H), 7.43-7.47 (m, 1 H), 8.47 (d, J = 3.60 Hz, 1 H). MS ESI calculated $C_{21}H_{21}F_4N_7O_3S$ [M + H]⁺ 528, found 528. Chiral column: OJ (250 mm*30 mm, 5 μm); mobile phase: [0.1% NH₃H₂O IPA]; B %: 30%-30%, 4.71 minutes. |
| 18 | 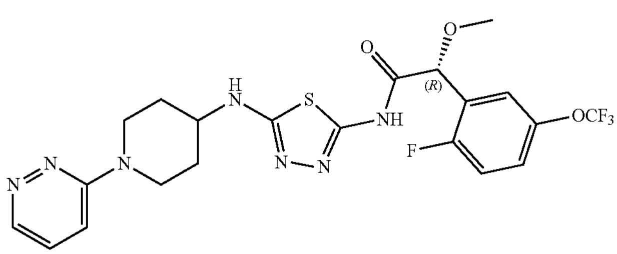 | ¹HNMR (400 MHz, METHANOL-d₄) δ ppm 1.40-1.53 (m, 2 H), 2.03-2.11 (m, 2 H), 3.06-3.17 (m, 2 H), 3.37 (s, 3 H), 3.75-3.85 (m, 1 H), 4.22 (br d, J = 13.80 Hz, 2 H), 5.15 (s, 1 H), 7.14-7.32 (m, 4 H), 7.35 (br d, J = 5.27 Hz, 1 H), 8.33-8.37 (m, 1 H). MS ESI calculated $C_{21}H_{21}F_4N_7O_3S$ [M + H]⁺ 528, found 528. Chiral column: OJ (250 mm*30 mm, 5 μm); mobile phase: [0.1% NH₃H₂O IPA]; B %: 30%-30%, 5.15 minutes. |

Experimental Example 1: Activity Test of Compounds in GLS1 Coupling Reaction System Reagents and instruments are as shown in Table 2:

TABLE 2

| Purpose | Name | Brand Article Number |
|---|---|---|
| Buffer | Tris-HCl (pH 8.0) | Invitrogen-15568025 |
| | EDTA | Sigma E 6758 |
| | $K_2HPO_4$ | Sigma-60353-250G |
| | DTT | Sigma-43815 |
| | Triton X-100 | Sigma-T9284-500 mL |
| Biochemical Experiment | $NAN^+$ | Sigma-N1636 |
| | L-Glutamine | Sigma-49419 |
| | Glutamate Dehydrogenase (GLDH) | Roche-10197734001 |
| | GLS-1, His-tag | BPS (BPS Bioscience)-71102 |
| | Adenosine diphosphate | Sigma-01905-250MG-F |
| | DMSO | Sigma-D2650 |
| Experimental plates | Grenier Bio-one microclear 384-well | Grenier-781091 Grenier-781090 |
| ECHO compound plates | Labcyte Echo rated 384 well polypropylene plates | Labcyte-LP0200 Labcyte-P05525 |
| Instruments | Labcyte ECHO 550 acoustic dispenser | Labcyte |
| | Multidrop Combi(Thermo) | Thermo |
| | Standard plastic tip dispensing cassette (Thermo) | Thermo-24072670 |
| | SpectraMax 340PC | |

Preparation of Reaction Reagents:
Relevant reagents should be prepared on the day of the experiment:
Preparation of 1× assay buffer
The final concentration of each component in the final experimental buffer was: 50 mM Tris-HCl pH 8.0, 0.25 mM EDTA, 150 mM $K_2HPO_4$, 0.1 mg/mL BSA, 1 mM DTT, 0.01% Triton X-100
Preparation of 2× experimental component solutions:
The reagents were taken out and placed on ice to melt naturally for later use;
1× assay buffer was used to prepare "solution A" (solution A contains: L-glutamine, NAD+(nicotinamide adenine dinucleotide) and GLDH (glutamic acid dehydrogenase)). The final concentrations of each component in the final experimental reaction system were 4.5 mM L-glutamine, 2 mM NAD+ 4 U/mL GLDH.
1× assay buffer was used to prepare "solution B" - - - 2× enzyme solution (solution B contains GLS1 enzyme). The final concentration of GLS1 in the final experimental reaction system was 2 nM.
Experimental Steps:
The experiment plates are prepared by Labcyte ECHO before the experiment, which contain the compounds gradient concentrations and the corresponding DMSO solution:
The experimental plates were taken out, and 20 μL of solution B (enzyme GLS1 solution) was added to columns 2 to 23 of the experimental plate, then 20 μL assay buffer was added to columns 1 and 24 as Min control in the experimental system.
Then the experimental plates were centrifuged at 1000 rpm for 30 seconds; and sealed the membrane, and the plates were incubated at 23° C. for 1 hour.
After the incubation of 1 hour, 20 μL of solution A was added to columns 1 to 24 of the experimental plates (ie, Samples were added to the whole plate).

The experimental plates were centrifuged at 1000 rpm for 30 seconds.

The experimental plates were placed on the SpectraMax 340PC, and the plates were continuously read for 20 minutes in dynamic mode (the reading interval was set to 1 minute).

Inhibitory activity results of compounds were shown in Table 3.

TABLE 3 inhibitory activity results of compounds

| Example | GLS1($IC_{50}$) |
|---|---|
| 5 | B |
| 7 | B |
| 8 | B |
| 9 | B |
| 16 | B |
| 17 | A |

* A < 200 nM; 200 nM ≤ B ≤ 1000 nM; C > 1000 nM

Experimental Conclusion:

The compounds designed by the present invention exhibited good GLS1 enzyme inhibitory activity.

Experimental Example 2: Evaluation of Compounds Pharmacokinetics

Experimental purpose: To test the pharmacokinetics of compounds in mice

Experimental Materials:

C57BL/6 mice (female, 7-9 weeks old, Shanghai SLAC)

Experimental procedure: C57BL/6 mice (C57BL/6) were administered a clear solution obtained by dissolving test compounds via tail vein injection and intragastric administration (overnight fast, 7-9 weeks old). After administration of the test compounds, the intravenous group was at 0.0833, 0.25, 0.5, 1, 2, 4, 6, 8 and 24 h, and the gavage group was at 0.0833, 0.25, 0.5, 1, 2, 4, 6, 8 and 24, blood was collected from the mandibular vein and centrifuged to obtain plasma. LC-MS/MS method was used to determine blood drug concentration, and WinNonlin™ Version 6.3 pharmacokinetic software was used to calculate the relevant pharmacokinetic parameters by non-compartment model linear logarithmic trapezoid method. The test results were as follows:

TABLE 4

PK test results of compounds in mice

| PK parameters | Example 2 | Example 17 |
|---|---|---|
| $T_{1/2}$ (hr) | 3.70 | 2.52 |
| $C_{max}$ (nM) | 11800 | 11600 |
| $AUC_{0-inf}$ (nM · hr) | 43931 | 26141 |
| Bioavailability (%)$^a$ | 58.7 | 91.3 |

Note:
$T_{1/2}$: half-life;
Cmax: maximum concentration;
$AUC_{0-inf}$: area under the plasma concentration-time curve from time 0 to extrapolation to infinity.

Conclusion: The compounds of the present invention had good oral bioavailability in mice or rats and higher exposures, which were conducive to producing good in vivo pharmacological efficacy.

Experimental Example 3 In Vivo Pharmacodynamics of Mouse Lung Cancer 3LL Cells Subcutaneous Xenograft Tumor C57/BL6 Nude Mouse Model Experimental purpose: To evaluate the efficacy of the compounds to be tested in a mouse lung cancer 3LL cells subcutaneous xenograft tumor C57/BL6 nude mouse model
Experimental animals: Female C57/BL6 nude mice, 6-8 weeks old, weight 18-22 g; supplier: Shanghai Lingchang Biotechnology Co., Ltd.
Experimental Method and Steps:
3.1 Cells Culture
Mouse lung cancer 3LL cells were cultured in monolayer in vitro at 37° C. with 5% $CO_2$. The culture conditions were RPMI-1640 medium plus 10% fetal bovine serum, 100 U/mL penicillin, 100 μg/mL streptomycin and 2 mM glutamine. Trypsin-EDTA was used twice a week for routine digestion treatment and passaging, when the cell saturation was 80%–90%, the cells were collected, counted, and inoculated.
3.2 Tumor Cells Inoculation (Tumor Inoculation)
0.1 mL of $2\times10^6$ 3LL cells were subcutaneously inoculated on the right back of each C57/BL6. Group administration was started when the average tumor volume reached 66 $mm^3$.
3.3 Preparation of Test Substance:
The test compound was formulated into a clear solution of 1 mg/mL, with a solvent of 0.2% Tween 80, 25% HPBCD (hydroxypropyl-β-cyclodextrin), 10 mM citrate buffer, pH=4. PD-1 (Bioxcell, batch number 5792-210715/665417S1) was added to the filtered PBS (phosphate buffer solution) and mixed well to obtain a clear solution of 8.25 mg/mL for later use. PD-L1 (Bioxcell, batch number: 66571701B/66571713) was added to the filtered PBS and mixed well to obtain a 5.5 mg/mL clear solution for later use.
3.4 Tumor Measurement and Experimental Indicators
The experimental indicators were to investigate whether tumor growth was inhibited, delayed or cured. The diameter of tumor was measured by vernier caliper twice a week. The calculation formula of tumor volume was as follows: $V=0.5a\times b^2$, a and b represent the long and short diameter of tumor respectively.
The antitumor effect of the compound was evaluated by TGI (%) or relative tumor proliferation rate T/C (%). TGI (%) reflected the tumor growth inhibition rate. Calculation of TGI (%):TGI (%)=[1−(average tumor volume at the end of administration in a treatment group-average tumor volume at the beginning of treatment in this treatment group)/ (average tumor volume at the end of treatment in a solvent control group− average tumor volume at the beginning of treatment in a solvent control group)]×100%.
Relative tumor proliferation rate T/C (%): the calculation formula is as follows: T/C %=$T_{RTV}/C_{RTV}\times100\%$ ($T_{RTV}$: average RTV in the treatment group; $C_{RTV}$: average RTV in the negative control group). The relative tumor volume is calculated based on the results of tumor measurement (relative tumor volume, RTV), the calculation formula is $RTV=V_t/V_0$, where $V_0$ is the tumor volume measured during group administration (ie, do), and $V_t$ is the value of one measurement tumor volume, $T_{RTV}$ and $C_{RTV}$ were taken on the same day.
3.5 Statistical Analysis
Statistical analysis included mean and standard error (SEM) of tumor volume at each time point in each group (see Table 5 for specific data). Statistical analysis was performed to assess differences between groups based on data on the $12^{th}$ day after administration. Comparisons between multiple groups were analyzed by one-way ANOVA and tested by Dunnet (2-sided) method. All data analysis was performed with SPSS 17.0. Significant differences were considered when p<0.05.
3.6 Daily Observation of Experimental Animals
In the experiment, the effect of the test compound on the body weight of the animal was examined. At the same time, the daily behavior activities of animals, water consumption (only visual inspection), appearance signs or other abnormal conditions were routinely checked. Animal deaths and side effects were recorded based on the number of animals in each group.
3.7 Experimental Results
3.7.1 Animals Weight
The body weight of experimental animals was used as a reference indicator for indirect determination of drug toxicity. All the administration groups in this model showed no significant weight loss, and no morbidity or death. The effect of the test substance on the body weight of the mouse lung cancer 3LL cells subcutaneous transplantation tumor female C57/BL6 nude mouse model was shown in FIG. 1.
3.7.2 Tumor Volume
The changes of tumor volume in each group after the administration of Example on female mouse C57/BL6 model of subcutaneously transplanted tumor of lung cancer 3LL cells was shown in Table 5.

TABLE 5

Evaluation of antitumor efficacy of example 17 on mouse lung cancer 3LL transplantation model (Calculated based on tumor volume on the $12^{th}$ day after administration)

| Group | Tumor volume $(mm^3)^a$ (Day 12) | $T/C^b$ (%) | $TGI^b$ (%) | p value$^c$ |
|---|---|---|---|---|
| Vehicle group | 2081 ± 387 | — | — | — |
| PD-1, (10 mg/kg) | 877 ± 292 | 40 | 60 | 0.000 |
| PD-L1, (10 mg/kg) | 1442 ± 319 | 65 | 32 | 0.110 |
| Example 17, 100 mg/kg(D 0-11) + 150 mg/kg(D 12-14) + PD-1, 10 mg/kg | 812 ± 95 | 39 | 63 | 0.000 |
| Example 17, 100 mg/kg(D 0-11) + 150 mg/kg(D 12-14) + PD-L1, 11 mg/kg | 934 ± 129 | 43 | 57 | 0.001 |

Note:
"—" referred to no calculation.
$^a$average ± SEM.
$^b$tumor growth inhibition was calculated by T/C and TGI (TGI (%) = [1 − ($T_{21}$ − $T_0$)/($V_{21}$ − $V_0$)] × 100).
$^c$p value was calculated according to tumor volume.

3.8 Conclusion

In a mouse lung cancer 3LL cells transplantation tumor model, the tumor volume of the tumor-bearing mice in the vehicle group reached 2081 $mm^3$ 12 days after the start of administration.

The tumor volume of PD-1 monotherapy group and PD-L1 monotherapy group were 877 $mm^3$, 1442 $mm^3$ respectively, T/C was 40%, 65% respectively, and p values were 0.000, 0.110.

After combination of test substance example 17 with PD-1 and PD-L1 respectively, the T/C was 39% and 43% respectively, and the p values were 0.000 and 0.001, both of which had significant tumor suppressive effects.

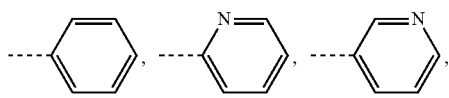

-continued
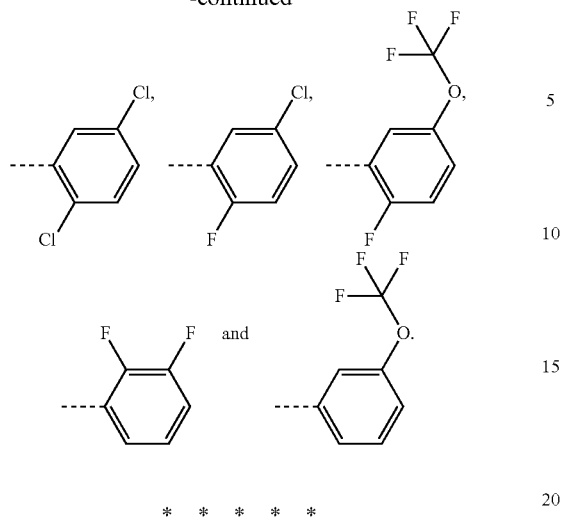

What is claimed is:

1. A compound represented by formula (I), an isomer thereof or a pharmaceutically acceptable salt thereof,

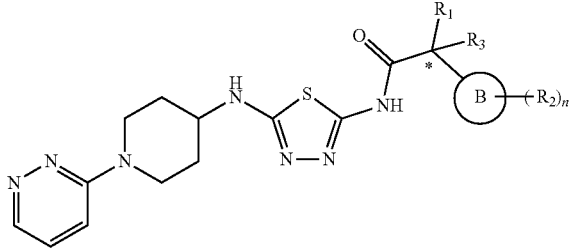

(I)

wherein, $R_1$ is selected from the group consisting of H, F, Cl, Br, I, OH, $NH_2$, $C_{1-6}$ alkyl and $C_{1-6}$ heteroalkyl, each of $C_{1-6}$ alkyl and $C_{1-6}$ heteroalkyl is optionally substituted by R, and the number of R is 1, 2 or 3;

$R_2$ is independently selected from the group consisting of H, F, Cl, Br, I, OH, $NH_2$, $C_{1-6}$ alkyl and $C_{1-6}$ heteroalkyl, each of $C_{1-6}$ alkyl and $C_{1-6}$ heteroalkyl is optionally substituted by R, and the number of R is 1, 2 or 3;

$R_3$ is selected from H;

or $R_1$ and $R_3$ are linked together with the carbon atom to which they are attached form a $C_{3-6}$ cycloalkyl;

ring B is selected from phenyl and 5-6 membered heteroaryl;

n is selected from 0, 1, 2 and 3;

R is selected from the group consisting of H, F, Cl, Br, I, OH, $NH_2$, $C_{1-6}$ alkyl and $C_{1-6}$ heteroalkyl, each of $C_{1-6}$ alkyl and $C_{1-6}$ heteroalkyl is optionally substituted by R', and the number of R' is 1, 2 or 3;

R' is selected from F, Cl, Br, I, OH and $NH_2$;

when $R_1$ is selected from H, or $R_1$ and $R_3$ are linked together with the carbon atom to which they are attached form a $C_{3-8}$ cycloalkyl, then the carbon atom with "*" is not a chiral carbon atom;

when $R_1$ is not selected from H, then the carbon atom with "*" is a chiral carbon atom, and the compound represented by formula (I) exists in the form of a single enantiomer of (R) or (S) or is enriched in one enantiomer;

the "hetero" of the $C_{1-6}$ heteroalkyl and 5-6 membered heteroaryl is selected from the group consisting of N, —O—, —S—, and —NH—;

the above number of heteroatoms or heteroatom groups is independently selected from 1, 2, 3, and 4.

2. The compound, the isomer thereof or the pharmaceutically acceptable salt thereof as defined in claim 1, wherein, R is selected from the group consisting of H, F, Cl, Br, I, OH, $NH_2$, $C_{1-3}$ alkyl and $C_{1-3}$ alkoxyl, each of $C_{1-3}$ alkyl and $C_{1-3}$ alkoxyl is optionally substituted by R', and the number of R' is 1, 2 or 3.

3. The compound, the isomer thereof or the pharmaceutically acceptable salt thereof as defined in claim 2, wherein, R is selected from the group consisting of H, F, Cl, Br, I, OH, $NH_2$, Me, Et and

, is optionally substituted by R', and the number of R' is 1, 2 or 3.

4. The compound, the isomer thereof or the pharmaceutically acceptable salt thereof as defined in claim 3, wherein, R is selected from the group consisting of H, F, Cl, Br, I, OH, $NH_2$, Me, $CF_3$, Et,

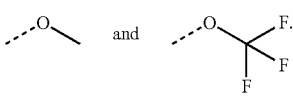

5. The compound, the isomer thereof or the pharmaceutically acceptable salt thereof as defined in claim 1, wherein, $R_1$ is selected from the group consisting of H, F, Cl, Br, I, OH, $NH_2$, $C_{1-3}$ alkyl and $C_{1-3}$ alkoxyl, each of $C_{1-3}$ alkyl and $C_{1-3}$ alkoxyl is optionally substituted by R, and the number of R is 1, 2 or 3.

6. The compound, the isomer thereof or the pharmaceutically acceptable salt thereof as defined in claim 5, wherein, $R_1$ is selected from the group consisting of H, F, Cl, Br, I, OH, $NH_2$, Me, $CF_3$, Et,

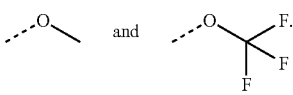

7. The compound, the isomer thereof or the pharmaceutically acceptable salt thereof as defined in claim 1, wherein, $R_2$ is independently selected from the group consisting of H, F, Cl, Br, I, OH, $NH_2$, $C_{1-3}$ alkyl and $C_{1-3}$ alkoxyl, each of $C_{1-3}$ alkyl and $C_{1-3}$ alkoxyl is optionally substituted by R, and the number of R is 1, 2 or 3.

8. The compound, the isomer thereof or the pharmaceutically acceptable salt thereof as defined in claim 7, wherein, $R_2$ is independently selected from the group consisting of H, F, Cl, Br, I, OH, $NH_2$, Me, $CF_3$, Et,

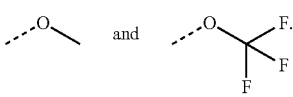

9. The compound, the isomer thereof or the pharmaceutically acceptable salt thereof as defined in claim 1, wherein, n is selected from 0, 1, and 2.

10. The compound, the isomer thereof or the pharmaceutically acceptable salt thereof as defined in claim 1, wherein, moiety

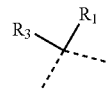

is selected from

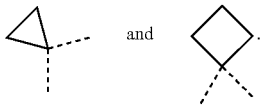

11. The compound, the isomer thereof or the pharmaceutically acceptable salt thereof as defined in claim 1, wherein, ring B is selected from phenyl and pyridine.

12. The compound, the isomer thereof or the pharmaceutically acceptable salt thereof as defined in claim 1, wherein, moiety

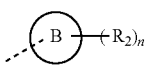

is selected from

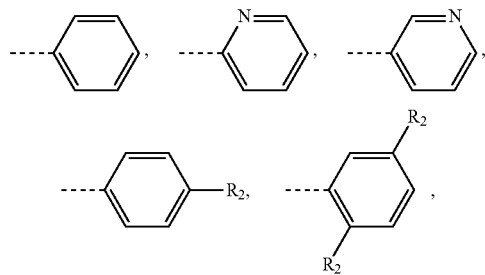

13. The compound, the isomer thereof or the pharmaceutically acceptable salt thereof as defined in claim 8, wherein, the moiety

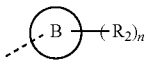

is selected from

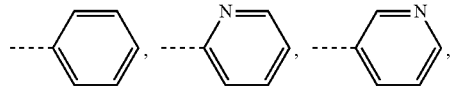

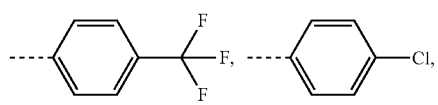

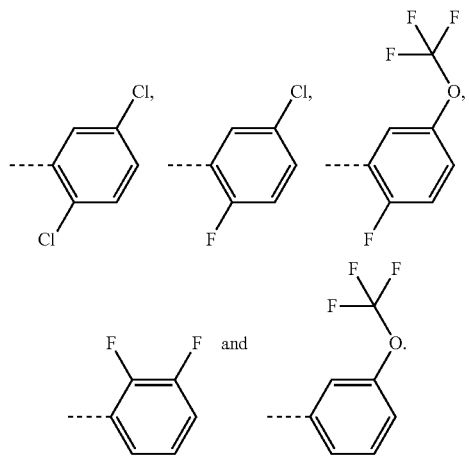

14. The compound, the isomer thereof or the pharmaceutically acceptable salt thereof as defined in claim 1, which is selected from

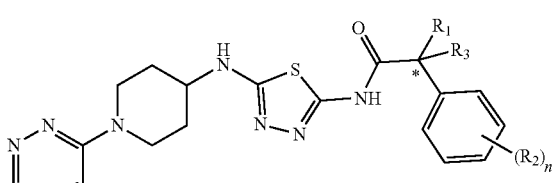

(I-1)

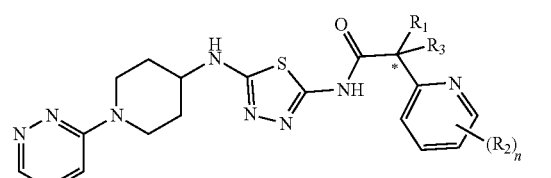

(I-2)

and

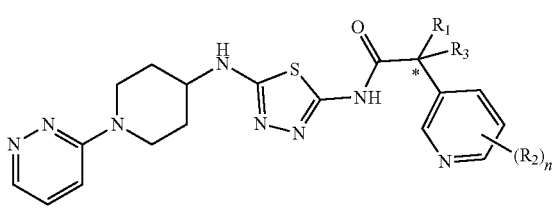

(I-3)

wherein, n, $R_1$, $R_2$, $R_3$ are as defined in claim 1;

when $R_1$ is selected from H, or $R_1$ and $R_3$ are linked together with the carbon atom to which they are attached form a $C_{3-6}$ cycloalkyl, then the carbon atom with "*" is not a chiral carbon atom;

when $R_1$ is not selected from H, then the carbon atom with "*" is a chiral carbon atom, and the compound represented by formula (I-1), (I-2) or (I-3) exists in the form of a single enantiomer of (R) or (S) or is enriched in one enantiomer.

15. Compounds as shown in the following formulae:

16. The compounds as defined in claim 15, which are selected from

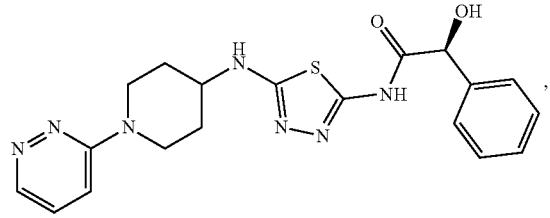

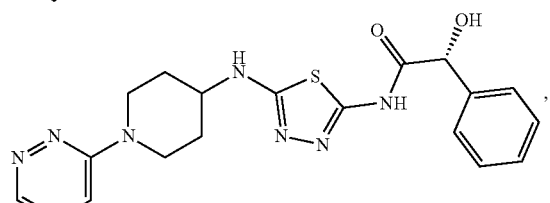

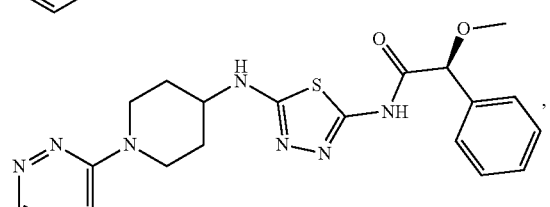

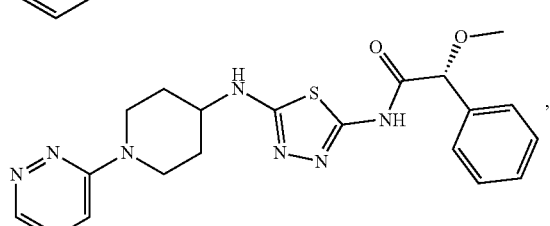

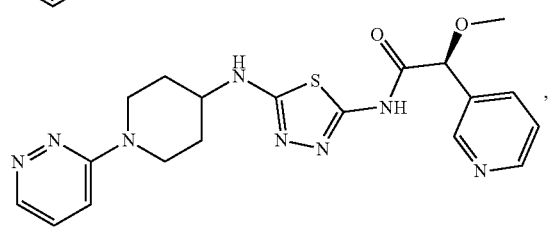

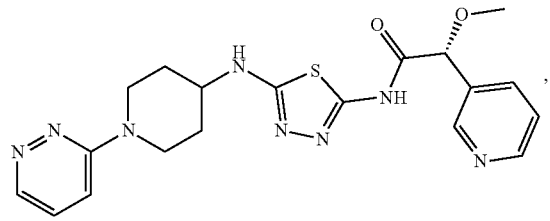

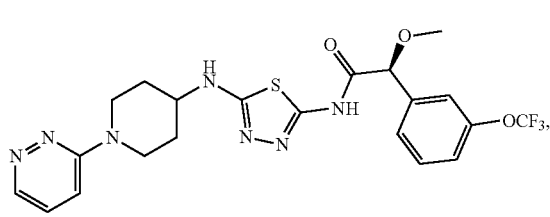

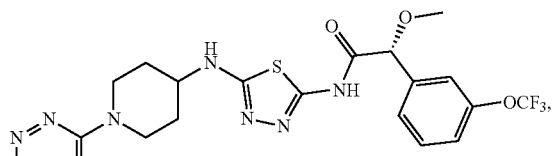

17. A pharmaceutical composition, comprising a therapeutically effective amount of the compound or the pharmaceutically acceptable salt thereof as defined in claim 1 as an active ingredient and a pharmaceutically acceptable carrier.

18. A method for treating GLS1 inhibitor related diseases in a subject in need thereof, comprising administering the compound or the pharmaceutically acceptable salt as defined in claim 1 to the subject:

wherein the GLS1 inhibitor related disease is lung cancer.

19. A method for treating GLS1 inhibitor related diseases in a subject in need thereof, comprising administering the pharmaceutical composition as defined in claim 17 to the subject:

wherein the GLS1 inhibitor related disease is cancer.

20. The compound, the isomer thereof or the pharmaceutically acceptable salt thereof as defined in claim 12, wherein, the moiety

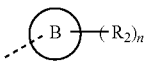

is selected from